US009447010B2

(12) United States Patent
Tverezovskiy et al.

(10) Patent No.: US 9,447,010 B2
(45) Date of Patent: Sep. 20, 2016

(54) METHOD FOR PREPARING A HERBICIDAL COMPOUND

(71) Applicant: BANGOR UNIVERSITY, Bangor (GB)

(72) Inventors: Viacheslav Vitalievich Tverezovskiy, Isle of Anglesey (GB); Radek Messias Braganca, Bangor (GB); Frank Arthur Howard, Cheshire (GB); Spencer Matthew Gould, Greater Manchester (GB); Paul Anthony Fowler, Stevens Point, WI (US); Mark Stephen Baird, Bangor (GB)

(73) Assignee: BANGOR UNIVERSITY, Gwynedd (GB)

( * ) Notice: Subject to any disclaimer, the term of this patent is extended or adjusted under 35 U.S.C. 154(b) by 0 days.

(21) Appl. No.: 14/378,121

(22) PCT Filed: Feb. 13, 2013

(86) PCT No.: PCT/GB2013/050323
§ 371 (c)(1),
(2) Date: Aug. 12, 2014

(87) PCT Pub. No.: WO2013/121190
PCT Pub. Date: Aug. 22, 2013

(65) Prior Publication Data
US 2015/0018569 A1    Jan. 15, 2015

(30) Foreign Application Priority Data
Feb. 13, 2012  (GB) .................................. 1202381.8

(51) Int. Cl.
| | | |
|---|---|---|
| *C07C 46/08* | (2006.01) | |
| *C07C 67/00* | (2006.01) | |
| *C07C 37/11* | (2006.01) | |
| *C07C 41/16* | (2006.01) | |
| *C07C 41/26* | (2006.01) | |
| *C07C 67/42* | (2006.01) | |
| *C07C 37/00* | (2006.01) | |
| *C07C 46/06* | (2006.01) | |
| *A01N 35/06* | (2006.01) | |
| *C07C 37/055* | (2006.01) | |
| *C07C 41/01* | (2006.01) | |
| *C07C 46/02* | (2006.01) | |

(52) U.S. Cl.
CPC .............. *C07C 46/08* (2013.01); *A01N 35/06* (2013.01); *C07C 37/003* (2013.01); *C07C 37/0555* (2013.01); *C07C 41/01* (2013.01); *C07C 41/16* (2013.01); *C07C 41/26* (2013.01); *C07C 46/02* (2013.01); *C07C 46/06* (2013.01); *C07C 67/00* (2013.01); *C07C 67/42* (2013.01)

(58) Field of Classification Search
CPC ....... C07C 41/16; C07C 46/06; C07C 67/00; C07C 41/26
See application file for complete search history.

(56) References Cited

U.S. PATENT DOCUMENTS 2,531,502 A  * 11/1950  De Groote ................ C09F 5/06
                                                        528/1
2006/0167107 A1* 7/2006 Kundu et al. ................. 514/617

FOREIGN PATENT DOCUMENTS

| CN | 101919417 A |   | 12/2010 |
|---|---|---|---|
| GB | 2450682 A | * | 1/2009 |
| WO | 2011138608 A2 |   | 11/2011 |
| WO | 2013026727 A1 |   | 2/2013 |

OTHER PUBLICATIONS

Zaragoza Dorwald, Side Reactions in Organic Synthesis, 2005, Wiley-VCH Verlag GmbH & Co. KGaA, Weinheim, Preface. p. IX.*
Barbosa et al, Quimica Nova, Preparation and Phytotoxicity of Sorgoleone Analogues, 2001, 24(6), pp. 751-755.*
Ouk et al, Green Chemistry, Dimethyl Carbonate and Phenols to Alkyl Aryl Ethers via Clean Synthesis, 2002, 4, pp. 431-435.*
Boongaling et al., "Fractionation, Derivatization and Termiticidal Activity of Cashew (*Anacardium occidentale* L.) Nut Shell Liquid Against the Philippine Milk Termite (*Coptotermes vastator* Light)," 2008, 1 page, The Philippine Agricultural Scientist, vol. 91, No. 4 (Abstract).
Paramashivappa et al., "Novel Method for Isolation of Major Phenolic Constituents from Cashew (*Anacardium occidentale* L.) Nut Shell Liquid," 2001, pp. 2548-2551, J. Agric. Food Chem., vol. 49.
Dayan et al., "Sorgoleone," 2010, pp. 1032-1039, Phytochemistry, vol. 71.
Barbosa et al., "Preparation and Phytotoxicity of Sorgoleone Analogues," 2001, pp. 751-755, Quim. Nova, vol. 24, No. 6.
Nimbal et al., "Herbicidal Activity and Site of Action of the Natural Product Sorgoleone," 1996, pp. 73-83, Pesticide Biochemistry and Physiology, Article No. 0011.
Wong et al., "Isolation, structural elucidation, and chemical synthesis of 2-hydroxy-3-octadecyl-5-methoxy-1,4-benzoquinone (irisoquin), a cytotoxic constituent of Iris missouriensis," 1985, 1 page, J. Pharm. Sci. (Abstract).
Baylis et al., "Long Chain Phenols. Part 17. The Synthesis of 5-[(ZZ)-Pentadec-8,11-dienyl]-resorcinol Dimethyl Ether, 'Cardol diene' Dimethyl Ether," 1981, pp. 132-141, Journal of the Chemical Society, Perkin Transactions.
Barrero et al., "Resorcinol Derivatives and Other Components of Ononis Speciosa," 1989, pp. 161-164, Phytochemistry, vol. 28, No. 1.

(Continued)

*Primary Examiner* — Paul A Zucker
(74) *Attorney, Agent, or Firm* — Hoffman Warnick LLC

(57) ABSTRACT

The present invention discloses a simple method for transforming cashew nut shell liquid into an active herbicidal composition.

18 Claims, 1 Drawing Sheet

(56) References Cited

OTHER PUBLICATIONS

Wasserman et al., "Cashew Nut Shell Liquid. III. The Cardol Component of Indian Cashew Nut Shell Liquid with Reference to the Liquid's Vesicant Activity," 1948, pp. 3675-3679, Journal of the American Chemical Society, vol. 70, No. 11.

Patent Cooperation Treaty, The International Search Report and the Written Opinion of the International Searching Authority, or the Declaration for PCT/GB2013/050323 dated Apr. 23, 2013, 17 pages.

\* cited by examiner

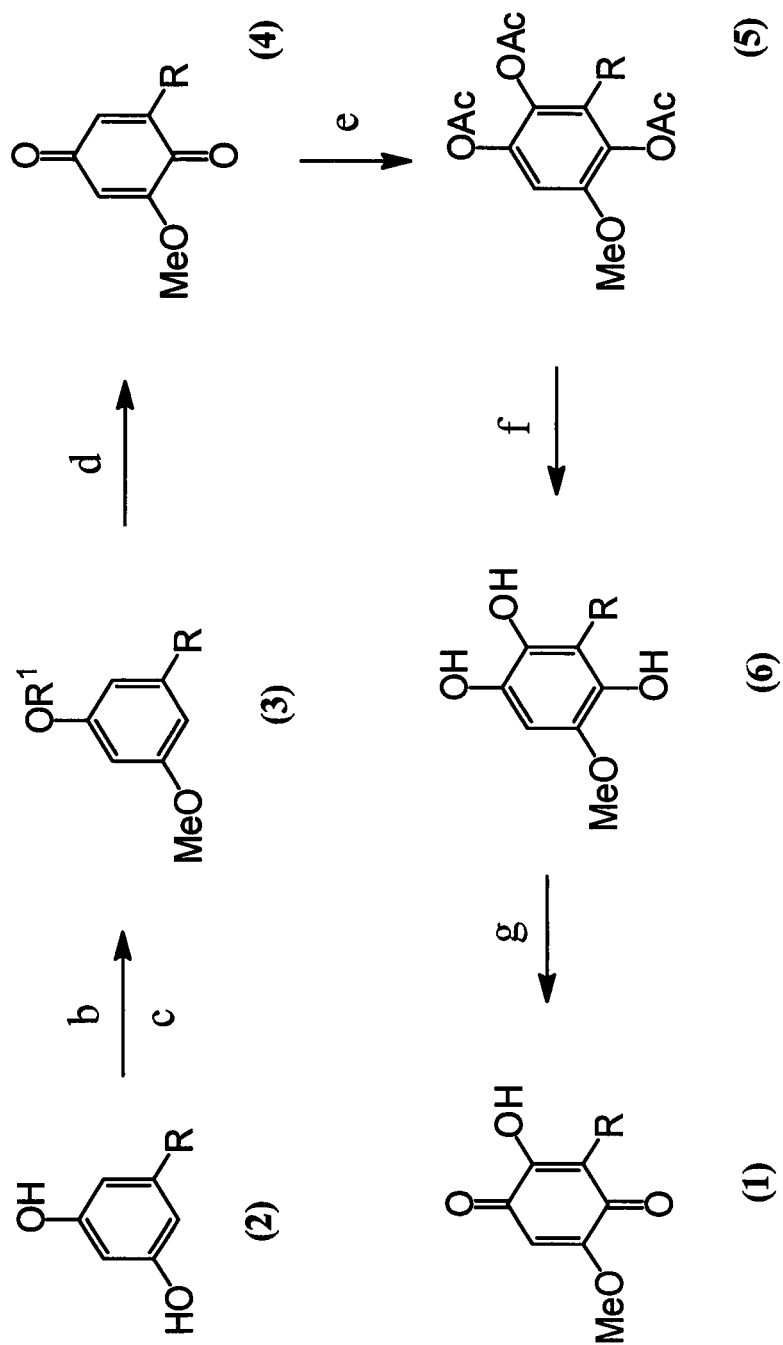

METHOD FOR PREPARING A HERBICIDAL COMPOUND

FIELD OF THE INVENTION

The present invention discloses a method for preparing a herbicidal compound.

DESCRIPTION OF THE RELATED ART

Several herbicidal compositions contain synthetic chemicals that, while being very efficient to suppress unwanted weeds, also introduce in the soil products that might contaminate crops and underground water reservoirs. It is therefore desirable to develop herbicides derived from natural products that do not require undesirable chemicals in their manufacture or degrade to undesirable chemicals in the soil.

It is known that root exudates of Sorghum (*Sorghum bicolor* (L.) Moench) have potent plant growth inhibiting properties, as disclosed for example in Dayan et al. (Dayan F. E., Cantrell C. L., and Duke S. O. in Bioorg. Med. Chem., 17, 4022, 2009). It was discovered by Kagan et al. (Kagan I. A., Rimando A. M. and Dayan F. E. in J. Agric. Food Chem., 51, 7589, 2003) that the main active component of the root exudate was sorgoleone (1a), together with minor components such as benzoquinones (1b, 1c and 1d) that differ from sorgoleone by the fact that they contain fewer double bonds in the otherwise same 15 carbon linear chain as seen in the following formulae:

(1a-d)

R =

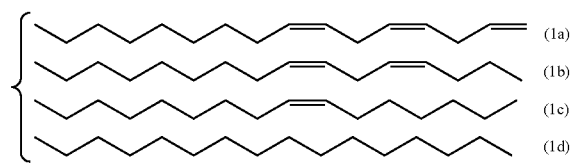

(1a)
(1b)
(1c)
(1d)

Sometimes all benzoquinones (1a-1d) are called Sorgoleones. For example, Dayan et al. call benzoquinone 1a—Sorgoleone-358, 1b—Sorgoleone-360, 1c—Sorgoleone-362 and 1d—Sorgoleone-364.

It has been observed for example by Kagan et al. that all allelochemicals (1a to 1d) have similar potent inhibition effect in spinach thylakoid membranes indicating that the level of saturation of the lipophilic side chain is not important for their allelopathic properties.

The only known chemical total synthesis of sorgoleone was achieved by Sargent and Wangchareontrakul (Sargent M. V. and Wangchareontrakul S., in J. Chem. Soc. Perkin Trans., 1, 1429, 1990 (first reported in *ibid, idem*, 1171, 1989)): it involves a total of 17 steps.

There is thus a need for an easy way to produce nature-identical or "nature-suggested" herbicides that are not detrimental to the environment. "Nature-suggested" herbicides herein means herbicides which are close in structure to the nature-identical herbicides described herein as structures 1a to 1d; in particular those compounds described or defined herein which are analogues or homologues of the compounds of structure 1a to 1d.

SUMMARY OF THE INVENTION

It is an objective of embodiments of the present invention to prepare a herbicidal compound.

It is another objective of embodiments of the present invention to transform an abundant and cheap natural compound into an active herbicidal compound.

It is also an objective of embodiments of the present invention to develop a simple and efficient method for preparing a herbicidal compound.

It is a further objective of embodiments of the present invention to develop nature-identical or nature-suggested herbicidal compounds.

It is yet a further objective of embodiments of the present invention to prepare non persistent, biodegradable herbicidal compounds.

Some or all of these objectives are realised in embodiments of the invention.

The present invention is defined in the independent claims. Preferred embodiments are defined in the dependent claims.

BRIEF DESCRIPTION OF THE DRAWINGS

These and other features of this invention will be more readily understood from the following detailed description of the various aspects of the invention taken in conjunction with the accompanying drawings that depict various embodiments of the invention, in which:

FIG. 1 shows a summary of a reaction scheme according to an embodiment of the invention.

The drawings are intended to depict only typical aspects of the invention, and therefore should not be considered as limiting the scope of the invention.

DETAILED DESCRIPTION OF THE INVENTION

Accordingly, the present invention discloses a method for preparing an active herbicidal compound comprising one or more compounds of general formula (1) and/or its precursor(s) of general formula (6)

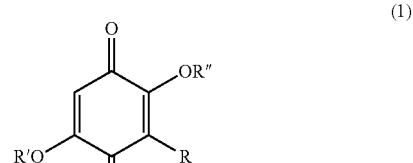
(1)

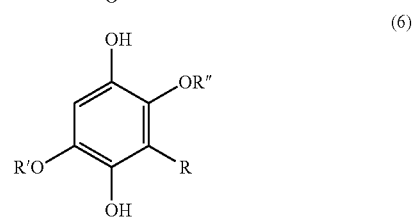
(6)

wherein R is a unsubstituted or substituted alkyl, alkenyl or alkynyl group, branched or unbranched, preferably unbranched, having from 5 to 22 carbon atoms, preferably from 12 to 18 carbon atoms and more preferably 15 carbon atoms and comprising 0, 1, 2, 3, 4 or 5 unsaturations, preferably double bonds, and wherein the substituents, if present, are selected from alkyl or aryl groups having up to 12 carbon atoms. It can also be a mixture of chains having the same length but different unsaturations, and/or different positions for the unsaturations, or a mixture of chains having different lengths or a mixture of chains having both different lengths and different unsaturations;

wherein R' is preferably selected from unsubstituted or substituted alkyl, alkenyl, alkynyl or acyl group, branched or unbranched, preferably unbranched, having from 1 to 10 carbon atoms, preferably from 1 to 5 carbon atoms and more preferably 1 carbon atom and comprising 0, 1, 2, or 3 unsaturations, preferably double bonds, and wherein the substituents, if present, are selected from alkyl or aryl groups having up to 12 carbon atoms. It can also be a mixture of chains having the same length but different unsaturations, and/or different positions for the unsaturations. The most preferred R' is methyl group;

and wherein R" is preferably selected from unsubstituted or substituted alkyl, alkenyl, alkynyl or acyl group, branched or unbranched, preferably unbranched, having from 1 to 10 carbon atoms, preferably from 1 to 5 carbon atoms and comprising 0, 1, 2, or 3 unsaturations, preferably double bonds, and wherein the substituents, if present, are selected from alkyl or aryl groups having up to 12 carbon atoms. It can also be a mixture of chains having the same length but different unsaturations, and/or different positions for the unsaturations. Most preferably R" is hydrogen atom.

Said method comprises the steps of:
a) starting from at least one compound of general formula (2) called cardol, suitably in purified form as extract

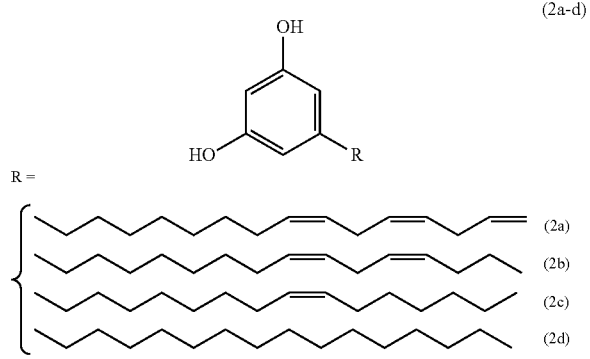

b) optionally hydrogenating the unsaturated carbon-carbon bonds in R;
c) alkylating the one or more compounds of step a) or of step b);
d) oxidising the one or more compounds obtained in step c);
e) Thiele (Thiele-Winter) acetoxylating the one or more compounds obtained in step d);
f) deacetylating the one or more compounds obtained in step e);
g) oxidising the one or more compounds obtained in step f) and isolating the active herbicidal compound.

The compound of general formula (2) may comprise one or more, for example one, two, three or all four of compounds (2a), (2b), (2c), and (2d). Suitably the compound of general formula (2) will contain compound (2a), and may optionally comprises any or each of compounds (2b), (2c), and (2d).

The use of precursor compound (6) instead of compound (1) offers the advantages of being more stable to store, of saving a manufacturing step and of starting oxidising in situ under most conditions once applied.

In the alkylation step, the form of group R' in final product (1) or (6), is determined by the nature of the alkylating agent, typically alcohol R'OH or alkyl halide R'X.

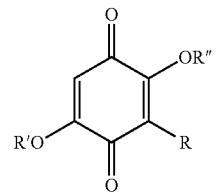
(1)

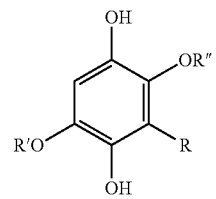
(6)

The starting material is typically and preferably selected from cardol (2). It can easily be extracted from cashew nut shell liquid (CNSL), itself a by-product of the cashew industry. CNSL is available in large amounts at a moderate cost. Solvent-extracted CNSL contains from 60 to 65 wt % of anacardic acid, 15 to 20 wt % of cardol about 10 wt % of cardanol and traces of methylcardol. Technical CNSL, obtained by roasting shells contains 60 to 65 wt % of cardanol, 15 to 20 wt % of cardol, 10 wt % of polymeric material and traces of methylcardol.

Kumar et al. (Kumar P. P., Paramashivappa P. J., Vithayathil P. J., Subba Rao P. V., and Shrinivasa Rao, in J. Agric. Food Chem., 50, 4705, 2002) claimed that cardol can be separated from cardanol by solvent extraction using for example a method where technical CNSL is dissolved in a mixture of methanol and ammonium hydroxide in a specific ratio of 8 to 5. Another method for extracting cardol from CNSL has been disclosed in co-pending British patent application GB1007472.2. The third method of separation of cardol and cardanol involves supercritical carbon dioxide and is described in co-pending application GB1114622.2.

Hydrogenation step b) is carried out under hydrogen, at a pressure of from 1 to 100 bars, preferably of from 1 to 5 bars, and in the presence of a catalyst. The catalyst is preferably selected from 5% Pd on charcoal, neat or in solution. The solvent, if present, is preferably selected from methanol, ethanol, isopropanol and n-propanol.

Alkylation step c) is carried out with any alkylating agent. Typical alkylating agents can be selected from alcohol R'OH or alkyl halide R'X, wherein R' is as described here above, preferably alkyl having up to 6 carbon atoms, more preferably methyl, and wherein X is halogen, preferably chlorine. The alkylating agent can also be selected from alkyl sulfonate, dialkylsulfate, dialkyl carbonate. Typically at least one equivalent of alkylation agent is used, preferably, at least 2 equivalents. If the reactants are in solid form, a solvent may be added. The reaction is carried out at a temperature ranging between 0 and 140° C., preferably between 50 and 130° C. more preferably at 120° C. The temperature depends upon the nature of the reactants used. In a most preferred embodiment according to the present invention the reaction is carried out at room temperature with a biphasic system comprising dimethylsulfate and petrol, or at a temperature ranging between 40 and 140° C. with dialkyl carbonate, preferably with dimethyl carbonate, in the presence of a phase transfer catalyst, such as tetraalkylammonium salts/ sodium carbonate.

Oxidation step d) is carried out with an oxidising agent. Typical oxidising agent can be selected from air, oxygen, hydrogen peroxide, $CrO_3$, potassium permanganate, ferric chloride, potassium dichromate or nitric acid. When air or oxygen is used, it is necessary to add an oxidation catalyst such as salcomine (N,N'-Bis(salicylidene)ethylenediamine-cobalt(II)), Pt, Pd, Ru, Zr or Rh. The reaction temperature ranges between 0 and 100° C., preferably between 15 and 80° C., more preferably, it is room temperature. Most preferably, the oxidation is carried out at room temperature with air, in the presence of salcomine acting as catalyst. When $CrO_3$ is used, the reaction is carried out in acetic acid/water mixture, temperature ranges between 0 and 80° C., preferably between 20 and 60° C., more preferably, at 50° C.

Thiele acetoxylation step e) is typically carried out by reacting the oxidised compounds of step d) with an acetoxylation agent preferably selected from acetic anhydride, and a catalyst preferably selected from sulfuric acid, triflic acid, bismuth triflate, acetic phosphoric anhydride or boron trifluoride, at a temperature ranging between 0 and 80° C., preferably, at room temperature. The Thiele (Thiele-Winter) acetoxylation reaction is carried out in the presence of a Lewis acid acting as catalyst. It is described for example in Thiele (J. Thiele, in *Chem. Ber,* 31, 1247, 1898).

Deacetylation step f) is preferably carried out by reacting the acetoxylated compounds of step e) with hydrochloric or another strong acid, or lithium aluminium hydride, or sodium borohydride, or sodium cyanoborohydride, optionally in the presence of a solvent such as tetrahydrofuran (THF). Alternatively, it can be carried out by reaction with hydrogen in the presence of a catalyst selected from Pt, Pd or Ru. The reaction temperature ranges between 0 and 80° C., and is preferably room temperature. Most preferably, the deacetylation reaction is carried out with hydrochloric or another strong acid such as sulfuric or p-toluenesulfonic acid in methanol.

Second oxidation step g) is carried out on the compound of step f) in order to obtain the final product. It uses typically the same reactants and reaction conditions as the first oxidation step. It can be carried out with oxygen, or hydrogen peroxide, or $CrO_3$, or potassium permanganate, or ferric chloride, or potassium dichromate, or nitric acid, or with air in the presence of a catalyst selected from salcomine, Pt, Pd, Ru, Zr or Rh. The reaction temperature ranges between 0 and 100° C., preferably between 15 and 80° C., more preferably, it is room temperature. The most preferred oxidising agents for this second oxidation is ferric chloride or oxygen and the reaction is carried out at room temperature.

In a preferred embodiment according to the present invention the method for preparing the active herbicidal compound comprises the steps of:
a) starting from at least one compound of general formula (2) in purified form as extract

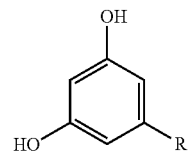

(2)

b) hydrogenating the unsaturated carbon-carbon bonds with hydrogen and Pd/C;
c) alkylating the one or more compounds of step b) with dimethylcarbonate;
d) oxidising the one or more compounds obtained in step c) with Chromium (VI) oxide;
e) Thiele (Thiele-Winter) acetoxylating the one or more compounds obtained in step d) with acetic anhydride/ sulfuric acid;
f) deacetylating the one or more compounds obtained in step e) with p-toluenesulfonic acid
g) optionally oxidising the one or more compounds obtained in step f) and isolating an active herbicidal compound The final product is sorgoleone in solution or its precursor (s)/derivative(s) in solution. It is retrieved from the solvent and cleaned from contaminant products using methods known in the art.

The compounds produced according to the present invention (Sorgoleone and its analogues) exhibit strong biocidal properties (JP09227307A). In addition to the expected herbicidal properties the compounds also exhibit: fungicidal (Suzuki. Y, Kono. Y, Inoue. T, Sakurai. A, Phytochemistry, 47, 997, 1998), algicidal (Uddin M R at al. Aquatic Botany, In Press, on line from December 2011) anticonvulsant (Mahendran S, at al. Phytomedicine. 2011 Jan. 15; 18(2-3): 186-8), antifouling (He W. et al. Biofouling 2001, 17:221-226) and antibacterial (Schrader. K. K, Toxins, 2, 1676, 2010) properties.

Compounds of this type can also act as antitumour and cytotoxic (Kubo, I; Chaudury, S K Biog. Med. Chem. Lett., 1994, 4, 1131-1134; Hu R, et al. Med Oncol. 2011 28(4) 1584-8), as anti-inflammatory (Mahendran S, at al. Chem Pharm Bull, 2011; 59(8):913-9) or as plant growth regulators (Einhellig. F. A, Souza, I. F, J. Chem. Ecol, 18. 1, 1992).

These compounds also mediate a range of enzyme activities including inhibition of mitonchondrial respiratory enzymes (Affourtit C at al. IUBMB Life. 2000 June; 49(6): 533-7) and 5-lipoxygenase inhibition (Haraguchi, H at al. Bioorg. Med. Chem. 1996, 4, 49-53, Fukuyama, at al. K. Chem. Pharm. Bull. 1993, 41, 561-565).

The present compounds can be used directly as produced, but they are typically used in the same forms as prior art biocides namely, wettable powders, dusts, emulsifiable concentrates, suspension concentrates, emulsion in water concentrate, soluble granules, insoluble granules, microencapsulations, oils, paints, varnishes, bitumen and resin based coatings, woven and non-woven impregnated fabrics, and coatings on other substrates such as paper, cardboard and wood. They may be incorporated into plastic materials and synthetic fibres during the moulding or extrusion process. They may be incorporated into waxes, minerals or natural organic materials such as vegetable oils, cereals etc.

The compounds prepared according to the present invention may be formulated as dry granules or powders by use of additives and carriers such as, but not limited to, fine mineral powder or granules such as diatomaceous earth, apatite, gypsum, talc, pyrophyllite, clay and silica of various types. Such mixtures may incorporate typical additives such as surface active agents, emulsifying agents, dispersing agents, stabilisers, antioxidants, coloured pigments/or dyes.

The present compounds may be formulated as non aqueous liquids under the form of solutions in solvents such as, for example aliphatic and aromatic hydrocarbons, alcohols, N Methyl Pyrrolidone, Piperonyl Butoxide, Dimethyl Sulfoxide, Tetrahydrofuran, Vegetable oils, Dimethyl Formamide, Dimethyl Acetamide or mixtures thereof. These solutions or mixtures of solutions may incorporate typical additives such as surface active agents emulsifying agents, dispersing agents stabilisers, antioxidants, coloured pigments/or dyes.

The compounds produced according to this invention may be formulated as aqueous products by dispersion, emulsification or solubilisation (as salts) into water, by absorption onto carriers dispersed in water, by formulation of microcapsule suspensions, by use of monomers or resins and suitable curing agents such as for example epoxy, polyurethane, acrylate, by dissolving in a suitable oil or solvent then emulsifying this concentrate into water. Likewise water soluble granules may be produced by blending with suitable water soluble waxes or surface active agents, carriers and inert material to produce a mixture suitable for both extrusion and pan granulation processes normally used for such formulations. These mixtures can incorporate typical additives such as surface active agents emulsifying agents, dispersing agents, stabilisers, antioxidants, coloured pigments/or dyes.

The present compounds can additionally be formulated into products suitable for coating or impregnation according to usual methods such as for example:

Anti-fouling paints and coatings for boats' and ships' hulls, said paints being based on natural and synthetic resins, bitumen, in both aqueous and solvent based formulations.

Wood preservatives for impregnating or coating timber to protect it from bacteria, fungus, termites, wood boring insects or marine worms.

Coatings for fabrics, paper or cardboard to provide biocidal protection against pests, said coatings being based on natural or synthetic resins, polymers, waxes or oils.

These product may additionally incorporate typical additives such as surface active agents emulsifying agents, dispersing agents stabilisers, antioxidants, coloured pigments/or dyes.

The present compounds are effective alone but can also be used in combination with other biocides both natural and synthetic including acaricides, insecticides, larvicides, termiticides, fungicides, herbicides, rodenticides, bactericides.

In accordance with a further aspect of the present invention there is provided the use of compounds (1) and/or (6) as defined above, obtained by the method of the present invention, to prepare compounds or compositions having herbicidal, biocidal, algicidal, insecticidal, termiticidal, nematicidal, larvicidal, molluscocidal, fungicidal, anticonvulsant, antifouling, antitumour, cytotoxic, antiinflamatory and antibacterial properties or capable of acting as plant growth regulators.

In accordance with a further aspect of the present invention there is provided the use of cardol to prepare sorgoleone and/or sorgoleone derivatives/analogues suitably as defined herein.

In accordance with a further aspect of the present invention there is provided the use of cashew nut shell liquid (CNSL) products to prepare an active herbicidal compound.

Preferably the cashew nut shell liquid (CNSL) products are cardol or any one or more of the compounds (2a), (2b), (2c) and (2d) defined herein.

Preferred features (for example preferred compounds, and preferred preparative methods) of the three 'use' aspects described above are preferred features of the other aspects of the invention, and are as set out above, and in the claims.

EXAMPLES

FIG. 1 shows a summary of a reaction scheme according to an embodiment of the invention.

In the reaction scheme of FIG. 1:
$R=C_{15}H_{31-2n}$ where n=0 to 3, R'=H or Me
Reagents and conditions are as follows: (b) $H_2$, Pd/C, 75° C.; (c) $(MeO)_2CO$, $Me_3BnN\ ^+OH^-$, reflux; (d) $CrO_3$, $AcOH/H_2O$, 50° C.; (e) $Ac_2O/H_2SO_4$, 32° C.; (f) $MeCN/H_2O$, PTSA, reflux; (g) $NaHCO_3$, $O_2$, 20° C.

Step b

Cardol (2.9 kg) and ethanol (3 L) were placed into a 10 L jacketed steel pressure reactor equipped with mechanical stirring, gas inlet, gas outlet and temperature probe. The reactor was vacuumed and nitrogen was introduced. The catalyst, 5% Pd/C (15 g) was added with stirring under nitrogen. Nitrogen was removed under vacuum and replaced by hydrogen. The reaction was kept with stirring at a temperature ranging between 60 and 75° C. under a pressure ranging between 6 and 7 bars of hydrogen during a period of time of 7 h. The excess hydrogen pressure was released at a temperature of 60° C., and the hydrogen atmosphere was changed into nitrogen atmosphere. The reaction mixture was filtered warm under nitrogen to yield after solvent removal 5-pentadecyl resorcinol (2d) (2.71 kg, 99%).

Step c

5-Pentadecyl resorcinol (10 g) was dissolved in dimethyl carbonate (40 ml), toluene (40 ml) and benzyltrimethylammonium hydroxide (7 ml, 40% wt in MeOH). Potassium carbonate (5 g) was added and the methanol was removed by distillation. After a period of time of 2 h at reflux high performance liquid chromatography (HPLC) showed 98% conversion to dimethoxycardol (3).

Step d

Dimethoxycardol (5 g) was dissolved in AcOH (20 ml). Chromium trioxide (2.88 g) was dissolved in 2 ml AcOH: 2 ml $H_2O$ and stirred for a period of time of 10 minutes at room temperature. The chromium trioxide solution was added to the saturated dimethoxycardol solution and the mixture stirred in the dark at a temperature of 50° C. After a period of time of 3 h the reaction mixture was cooled to room temperature and poured into water (100 ml) and extracted with dichloromethane (3×50 ml). The combined organic layers were washed with saturated bicarbonate solution (2×100 ml) and water (100 ml), dried (MgSO4) filtered and evaporated to yield benzoquinone (4) as an orange solid (3.5 g).

Step e

The benzoquinone (4) (2 g) was dissolved in acetic anhydride (5 ml) and concentrated sulfuric acid (0.5 ml) was added slowly. The mixture was stirred in the dark at a temperature of 32° C. and monitored by HPLC. After a period of time of 44 h, the reaction was worked up by pouring into iced water (50 ml) and extracting with dichloromethane (3×20 ml). The combined organics were washed with bicarbonate solution (3×50 ml), water (100 ml), dried ($MgSO_4$), filtered and evaporated to yield triacetate (5) which solidified (1.78 g).

Steps f and q

The triacetate (5) (50 g) was dissolved in MeCN (200 ml) and water (50 ml). p-toluenesulphonic acid (PTSA) (10 g) was added and the mixture was stirred at reflux. After a period of time of 1 h, a further 50 ml of water was added. After another period of time of 2 h, a further 50 ml of water was added and a further 10 g of PTSA was also added. The mixture was stirred for a total period of 24 h.

The reaction was cooled to room temperature and sodium bicarbonate was added in portions (16 g). Oxygen was then bubbled through the mixture in the dark for a period of time of 1 h. No precipitate was observed. A further 4 g of sodium bicarbonate was added. The mixture was then bubbled for a period of time of 4 hours with addition of MeCN to maintain constant volume during bubbling. Dichloromethane (200 ml) was added to dissolve the precipitate and the reaction was poured into water (400 ml) and extracted with dichloromethane (2×200 ml). The combined organic layers were washed with sodium bicarbonate solution (200 ml), water (200 ml), dried (MgSO4), filtered and evaporated to yield Sorgoleone (1d) as an orange solid (32.4 g).

The invention claimed is:

1. A method for preparing an active herbicidal compound comprising one or more compounds of general formula (1) and/or its precursor(s) of general formula (6)

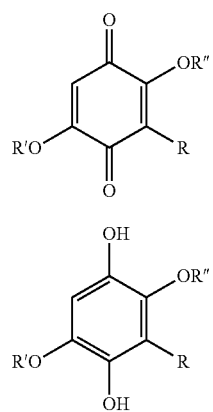

wherein R is an alkyl or alkenyl group having 12 to 18 carbon atoms, and having 0, 1, 2, or 3 unsaturations;
wherein R' is an alkyl group having from 1 to 5 carbon atoms; and
wherein R" is hydrogen or an alkyl having from 1 to 5 carbon atoms,
said method comprising the steps of:
a) starting from at least one compound of general formula (2) in purified form as extract (2)

b) alkylating the at least one compound of step a);
c) oxidising the at least one compound obtained in step b);
d) Thiele (Thiele-Winter) acetoxylating the at least one compound obtained in step c); and
e) deacetylating the at least one compound obtained in step d).

2. The method of claim 1 wherein R is alkyl having from 12 to 18 carbon atoms.

3. The method of claim 1 wherein the at least one compound of general formula (2) is cardol or any one or more of the following compounds:

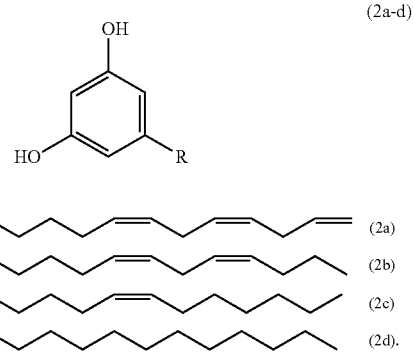

4. The method of claim 1 wherein alkylation step b) is carried out with alcohol R'OH wherein R' is alkyl having up to 6 carbon atoms, or with alkyl halide R'X wherein X is halogen, or with alkyl sulfonate or alkyl sulfate, or dialkyl sulfate, optionally in a solvent.

5. The method of claim 4 wherein the alkylation step b) is carried out with dialkyl carbonate in the presence of a phase transfer catalyst.

6. The method of claim 1 wherein first oxidation step c) is carried out with oxygen, or hydrogen peroxide, or $CrO_3$, or potassium permanganate, or ferric chloride, or potassium dichromate, or nitric acid, or with air in the presence of a catalyst selected from salcomine, Pt, Pd, Ru, Zr or Rh.

7. The method of claim 1 wherein Thiele (Thiele-Winter) acetoxylation step d) is carried out with acetic anhydride in the presence of sulfuric acid, or triflic acid, or bismuth triflate, or acetic phosphoric anhydride or boron trifluoride.

8. The method of claim 1 wherein deacetylation step e) is carried out with lithium aluminium hydride or in the presence of a Lewis acid or with hydrochloric or another strong acid like sulphuric or para-toluenesulfonic acids in polar solvent.

9. A composition comprising compounds (1) and/or (6) obtained by the method of claim 1, wherein the composition has herbicidal, biocidal, algicidal, insecticidal, termiticidal, nematicidal, larvicidal, mollusocidal, fungicidal, anticonvulsant, antifouling, antitumour, cytotoxic, antiinflamatory, or antibacterial properties.

10. The method of claim 1, further comprising:
hydrogenating the unsaturated carbon-carbon bonds of the at least one compound of general formula (2).

11. The method of claim 10, further comprising:
alkylating the hydrogenated at least one compound of general formula (2).

12. The method of claim 1, further comprising:
oxidising the one or more compounds obtained in step e) and isolating an active herbicidal compound.

13. A composition comprising compounds (1) and/or (6) obtained by the method of claim 1, wherein the composition is capable of acting as a plant growth regulator.

14. The method of claim 5, wherein R' is methyl and the dialkyl carbonate is dimethyl carbonate.

15. The method of claim 1, wherein the 1, 2, or 3 unsaturations includes at least one double bond.

16. A method for preparing an active herbicidal compound comprising one or more compounds of general formula (1) and/or its precursor(s) of general formula (6)

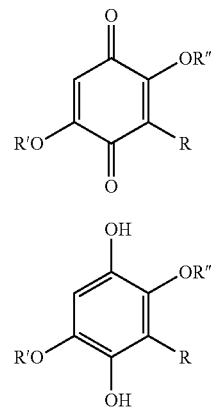

wherein R is $C_{15}H_{31-2n}$, where n is 0 to 3, R' is methyl, and R" is hydrogen, the method comprising:

a) starting from at least one compound of general formula (2);

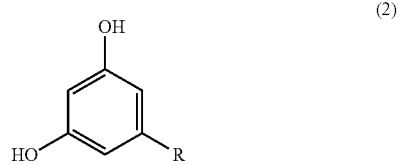

b) alkylating the at least one compound of step a);
c) oxidising the at least one compound obtained in step b);
d) Thiele (Thiele-Winter) acetoxylating the at least one compound obtained in step c); and
e) deacetylating the at least one compound obtained in step d).

17. The method of claim 12 wherein the oxidizing is carried out with ferric chloride.

18. The method of claim 12 wherein the oxidizing is carried out with oxygen or air in the presence of a catalyst selected from Pt, Pd, Ru, Zr or Rh.

* * * * *